US009970051B2

(12) United States Patent
Lee et al.

(10) Patent No.: US 9,970,051 B2
(45) Date of Patent: May 15, 2018

(54) SYSTEM FOR DIAGNOSING AVELLINO CORNEAL DYSTROPHY

(75) Inventors: Gene Lee, Gyeonggi-do (KR); Jung Kuk Yun, Seoul (KR)

(73) Assignee: AVELLINO CO., LTD., Seoul (KR)

( * ) Notice: Subject to any disclaimer, the term of this patent is extended or adjusted under 35 U.S.C. 154(b) by 0 days. days.

(21) Appl. No.: 13/876,603

(22) PCT Filed: Sep. 30, 2011

(86) PCT No.: PCT/KR2011/007272
§ 371 (c)(1),
(2), (4) Date: Jun. 14, 2013

(87) PCT Pub. No.: WO2012/044121
PCT Pub. Date: Apr. 5, 2012

(65) Prior Publication Data
US 2013/0302811 A1    Nov. 14, 2013

(30) Foreign Application Priority Data

Oct. 1, 2010    (KR) .................. 10-2010-0096103

(51) Int. Cl.
*C12Q 1/68* (2018.01)

(52) U.S. Cl.
CPC .......... *C12Q 1/686* (2013.01); *C12Q 1/6883* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,018,713 A | 1/2000 | Coli et al. | |
| 6,171,112 B1 | 1/2001 | Clark et al. | |
| 6,331,276 B1 | 12/2001 | Takei et al. | |
| 2003/0176650 A1 | 9/2003 | Grosse et al. | |
| 2003/0204418 A1 | 10/2003 | Ledley | |
| 2003/0211500 A1 | 11/2003 | Woosley | |
| 2004/0217345 A1 | 11/2004 | Boland et al. | |
| 2004/0263853 A1 | 12/2004 | Hill et al. | |
| 2005/0019757 A1 | 1/2005 | Stolarchuk | |
| 2006/0038990 A1 | 2/2006 | Habib et al. | |
| 2006/0057604 A1 | 3/2006 | Chen et al. | |
| 2006/0066249 A1 | 3/2006 | Wark et al. | |
| 2007/0254296 A1 | 11/2007 | Jiang et al. | |
| 2007/0274895 A1 | 11/2007 | Jesih et al. | |
| 2008/0113344 A1 | 5/2008 | Wirtz et al. | |
| 2008/0174775 A1 | 7/2008 | Moskovits et al. | |
| 2008/0267946 A1 | 10/2008 | Kim et al. | |
| 2009/0073447 A1 | 3/2009 | Dahint et al. | |
| 2009/0305394 A1 | 12/2009 | Lee et al. | |
| 2010/0190158 A1 | 7/2010 | Peitz et al. | |
| 2011/0053794 A1 | 3/2011 | Zhang | |
| 2012/0231537 A1 | 9/2012 | Templeton et al. | |
| 2013/0302811 A1 | 11/2013 | Lee et al. | |

FOREIGN PATENT DOCUMENTS

| | | |
|---|---|---|
| CN | 101144812 A | 3/2008 |
| CN | 101374850 A | 2/2009 |
| EP | 1715326 A1 | 10/2006 |
| EP | 1 964 606 A1 | 9/2008 |
| EP | 2 019 309 A2 | 1/2009 |
| JP | 2006-250668 A | 9/2006 |
| JP | 2009-045057 A | 3/2009 |
| JP | 2009-523442 A | 6/2009 |
| KR | 10-2007-0076532 A | 7/2007 |
| WO | WO 00/58509 A2 | 10/2000 |
| WO | WO 2005/015198 A1 | 2/2005 |
| WO | WO 2005/040756 A2 | 5/2005 |
| WO | WO 2005/114298 A2 | 12/2005 |
| WO | WO 2007/002567 A2 | 1/2007 |
| WO | WO 2007/083928 A1 | 7/2007 |
| WO | WO 2008/089280 A2 | 7/2008 |
| WO | WO 2012044121 A2 | 4/2012 |
| WO | WO 2015/073978 A2 | 5/2015 |

OTHER PUBLICATIONS

Han et al. Eye & Contact Lens vol. 36 No. 5 Sep. 2010.*
NCBI Reference Sequence NM_000358.2.*
Afshari, N., et al., "Survey of Patients With Granular, Lattice, Avellino, and Reis-Buecklers Corneal Dystrophies for Mutations in the BIGH3 and Gelsolin Genes", "Arch Ophthalmol.", 2001, pp. 16-22, vol. 119.
Dolmetsch, A., et al., "Combined granular-lattice corneal dystrophy (Avellino) in a patient with no known Italian ancestry","Can. J. Ophthalmol.", 1996, pp. 29-31, vol. 31, No. 1.
Holland, E., et al., "Avellino corneal dystrophy. Clinical manifestations and natural history", "Ophthalmology", 1992, pp. 1564-1568, vol. 99, No. 10.
Jun, R., et al., "Avellino Corneal Dystrophy After Lasik", "Ophthalmology", 2004, pp. 463-468, vol. 111.
Kennedy, S., et al., "Combined granular lattice dystrophy (Avellino corneal dystrophy)", "Br. J. Ophthalmol.", 1996, pp. 489-490, vol. 80.
Stewart, H., et al., "Heterogeneity in granular corneal dystrophy: Identification of three causative mutations in the TGFBI (BIGH3) gene-lessons for corneal amyloidogenesis", "Hum. Mutat.", 1999, pp. 126-132, vol. 14.
Avellino Co. Ltd., Notification of Grant, CN201180056997.7, dated Jul. 16, 2015, 5 pgs.
Avellino Lab USA Inc., International Preliminary Report on Patentability, PCT/US2014/029466, dated Jul. 14, 2014, 11 pgs.
Korea Advanced Institute of Science and Technology et al., Invitation Pursuant to Rule 62a(1) EPC, EP10810154.4, dated Sep. 1, 2015, 2 pgs.
Armelao, L., et al., "Innovative metal oxide-based substrates for DNA Microarrays," Inorganica Chimica Acta, Apr. 10, 2008, vol. 361, No. 12-13, pp. 3603-3608.

(Continued)

Primary Examiner — Joseph Woitach
(74) Attorney, Agent, or Firm — Morgan, Lewis & Bockius LLP

(57) ABSTRACT

The present invention relates to a system for diagnosing Avellino corneal dystrophy, and more particularly to a system for diagnosing Avellino corneal dystrophy, in which whether a sample is normal or Avellino corneal dystrophy is determined based on the ratio of the input first PCR amplification value and the second PCR amplification value. The system makes it possible to diagnosis Avellino corneal dystrophy in a simpler and accurate manner without being influenced by the doctor's skill. Particularly, the inventive system makes the overall process systematic, and thus provides accurate diagnosis. In addition, the system can also easily administer a number of test subjects.

20 Claims, 6 Drawing Sheets

(56) References Cited

OTHER PUBLICATIONS

Avelino Co. Ltd., European Search Report of application No. 14186678.0, dated Feb. 18, 2015, 5 pgs.
Avellino Lab USA Inc., International Search Report and Written-Opinion, PCTUS201465975, dated May 18, 2015, 19 pgs.
Database Genbank, Dec. 10, 1997, Database accession No. AF035627, 2 pgs.
GenBank Accession No. AF035627, "*Homo sapiens* mutant kerato epithelin (BIGH3) Gene, exon 4, partial cds," [retrieved on-line: http://www.ncbi.nlm.nih.gov/nuccore/AF035627.1, retrieval date, Sep. 7, 2013], published date Dec. 10, 1997, 1 pg.
Grove, D.S., "Quantitative Real-Time Polymerase Chain Reaction for the Core Facility Using TaqMan and the Perkin-Elmer/Applied Biosystems Division 7700 Sequence Detector," Journal of Biomolecular Techniques, Mar. 1999, vol. 10, pp. 11-16.
Huerva et al., "Role of BIGH3 R124H mutation in the diagnosis of Avellino corneal dystrophy," European Journal of Ophthalmology, May 2008, vol. 18, No. 3, pp. 345-350.
Kim, Jeong Wan et. al., "Anesthetic experience for patients with malignant gyperthermia susceptibility determined by molecular genetic test," J Korean Ophthalmol Soc vol. 49, No. 9, 2008, pp. 1431-1436.
Miller, S., et al., "A Simple Salting Out Procedure for Extracting DNA from Human Nucleated Cells," Nucleic Acids Research, 1998, pp. 1215, vol. 16, No. 3, Accepted for publication Jan. 19, 1996, 2 pgs.
Paliwal et al., Heterozygous Change T>G in the Sequence of Exon 12 of TGFBI Gene Seen in a Patienet with Corneal Dystrophy, Genbank :GQ368823.1, National Center for Biotechnology Information, Genbank, Jul. 28, 2009. 6 pgs.
Romero, P. et al., "Anticipation in familial lattice corneal dystrophy type I with R124C mutation in the TGFBI {BIGH3) gene," Molecular Vision vol. 14, May 7, 2008, pp. 829-835.
Strum, J.C. et al., "Tissue expression profiling using real-time PCR," Curr Protoc Pharmacol Nov. 2002; Chapter 6:Unit 6.9. DOI: 10.1002/0471141755.PH0609S18., 9 pgs.
Wittwer, Carl T., et al., "Real-Time Multiplex PCR Assays," 2001, Department of Pathology, University of Utah, School of Medicine, Salt Lake City, Utah 84132, 13 pgs.
Yoo, So Young et al., "Development of a DNA chip for the diagnosis of the most common corneal dystrophies caused by mutations in the high 3 gene," Br J Ophthalmol vol. 91, Jan. 10, 2007, pp. 722-727.
Yoshida, S., et al., "An analysis of BIGH3 mutations in patients with corneal dystrophies in the Kyushu district of Japan," JPN J Ophthalmol. Jul.-Aug. 2002;46(4):469-71, 3 pgs.

Zheng, Y. B., et al., "Surface plasmons of metal nanostructure arrays: from nanoengineering to active plasmonics," Jul. 9, 2008, Journal of the Association for Laboratory Automation, vol. 13, No. 4, pp. 215-226.
Chakravarthi, TGFBI Gene Mutations Causing Lattice and Granular Corneal Dystrophies in Indian Patients, Investigative Ophthalmology & Visual Science, Jan. 2005, vol. 46, No. 1, 5 pgs.
Halfon, P., et al., "Detection of IL28B SNP DNA from Buccal Epithelial Cells, Small Amounts of Serum and Dried Blood Spots," Mar. 2012, Plos ONE, vol. 7, Issue 3, Article No. e33000, pp. 1-6.
Kephart, D., "Rapid Isolation of Genomic DNA from Small Quantities of Human Tissue," 1999, Profiles in DNA, vol. 2, No. 3, pp. 7-9.
Cao W. et al., "Comparison of Methods for DNA Extraction from Paraffin-Embedded Tissues and Buccal Cells," Cancer Detection and Prevention, Elsevier Science, NL, vol. 27, No. 5, Jan. 1, 2003, 8 pgs.
Endo T et al., "Label-Free Detectionof Peptide Nucleic Acid-DNA Hybridization Using Localized Surface Plasmon Resonance Based Optical Biosensor," Analytical Chemisty, American Chemical Society, US, vol. 77, No. 21, 8 pgs.
Lee, Office Action, U.S. Appl. No. 14/454,669, dated May 5, 2016, 12 pgs.
Lounsbury Jenny et al., "Enhanced Recovery of Spermatozoa and Comprehensive Lysis of Epithelial Cells from Sexual Assault Samples Having a Low Cell Counts for Aged Up to One Year," Forensic Science International: Genetics, vol. 8, No. 1, Jan. 2014, 6 pgs.
Morbini Patrizia et al., "Oral HPV Infection and Persistence in Patients with Head and Neck Cancer," Oral Surgery, Oral Medicine, Oral Pathology and Oral Radiology, vol. 116, No. 4, Oct. 2013, 11 pgs.
Neuhaus, T., et al., "Reliability of Non-Invasively Acquired Human Genomic DNA as a Substrate for Real-Time PCR-Assisted Analysis of Genetic Polymorphisms," Archives of Toxicology, vol. 78, No. 7, Jul. 1, 2004, 7 pgs.
Beer etal., On-Chip, Real-Time, Single-Copy Polymerase Chain Reaction in Picoliter Droplets, 2007, Analytical Chemistry 79 (22): 8471, 5 pgs.
Chao-Shern, Office Action, U.S. Appl. No. 14/788,572, dated Dec. 16, 2016, 14 pgs.
Lee, Final Office Action, U.S. Appl. No. 14/454,669, dated Feb. 22, 2017, 14 pgs.
Lee, Office Action, U.S. Appl. No. 14/472,325, dated Dec. 19, 2016, 18 pgs.
Richards, et al., Multiplex PCR Amplification from the CFTR Gene Using DNA Prepared from Buccal Brushes/Swabs, 1993, Human Molecular Genetics 2 (2): 159-163, 5 pgs.
Walker et al., Collection of Genomic DNA by Buccal Swabs for Polymerase Chain Reaction-Based Biomaker Assays, 1999, Environmental Health Perspectives 107 (7): 517, 4 pgs.

\* cited by examiner

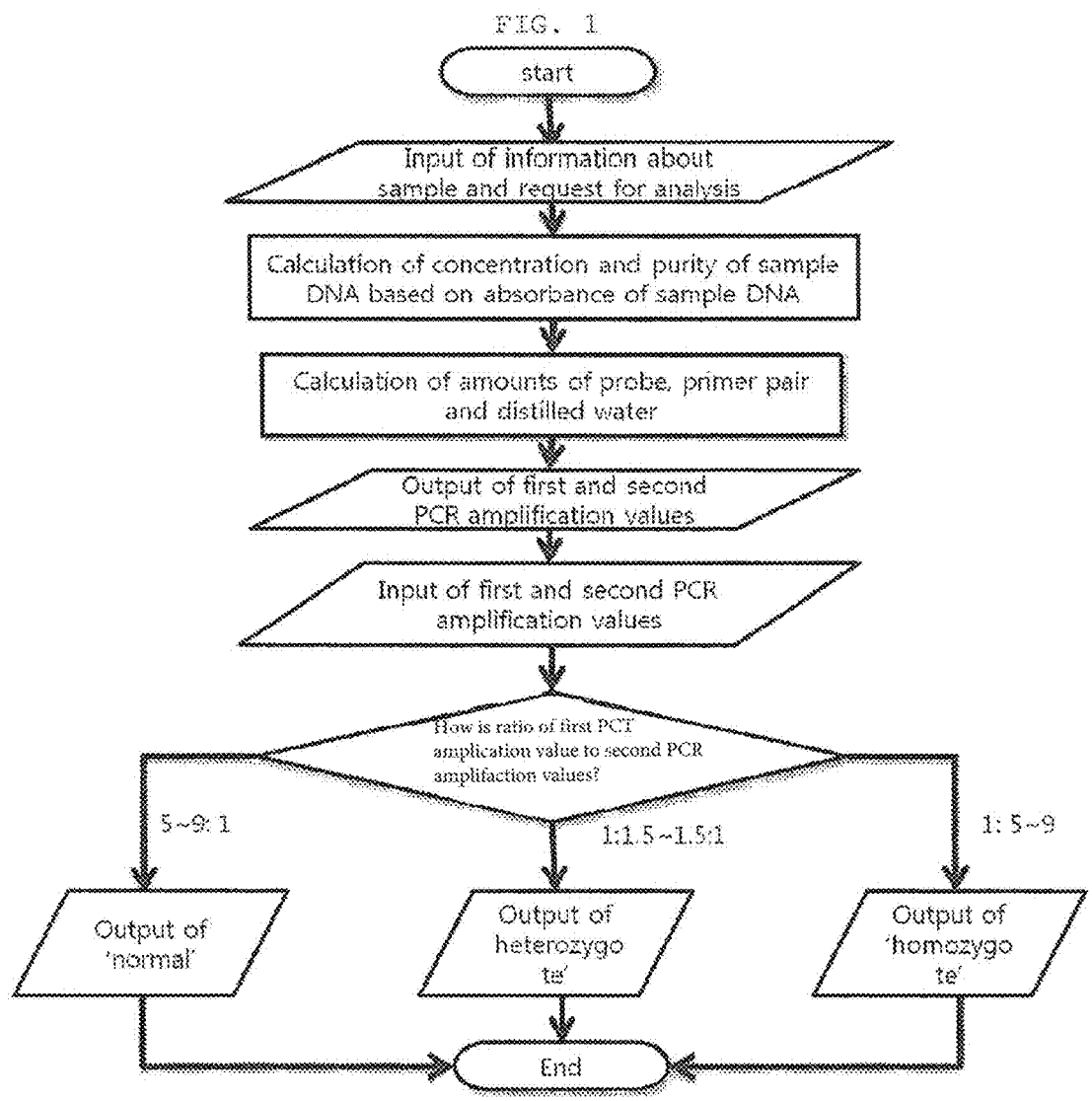

FIG.2

| No. | Sample ID | subject's name | analysis code | kind of sample | | | day and time of collection | remarks |
|---|---|---|---|---|---|---|---|---|
| | | | | whole blood(ml) | oral epidermis(number) | hair root(number) | | |
| 1 | KBS-6390 | 한*아 | ACD10-5899 | | | ✓ | 2010-02-13 12:08:37 | |
| 2 | KBS-6391 | 한*수 | ACD10-5900 | | | ✓ | 2010-02-13 12:11:27 | |
| 3 | KBS-6392 | 송*영 | ACD10-5901 | | | ✓ | 2010-02-13 12:27:10 | |
| 4 | KBS-6393 | 진*나 | ACD10-5902 | | | ✓ | 2010-02-13 12:30:35 | |
| 5 | KBS-6394 | 윤*님 | ACD10-5903 | | | ✓ | 2010-02-13 12:53:40 | |
| 6 | KBS-6395 | 박*나 | ACD10-5904 | | | ✓ | 2010-02-13 12:56:29 | |
| 7 | KBS-6396 | 홍*영 | ACD10-5905 | | | ✓ | 2010-02-13 13:04:17 | |
| 8 | KBS-6397 | 나*영 | ACD10-5906 | | | ✓ | 2010-02-13 13:08:38 | |
| 9 | KBS-6398 | 이*태 | ACD10-5907 | | | ✓ | 2010-02-13 13:11:37 | |
| 10 | KBS-6399 | 지*서 | ACD10-5908 | | | ✓ | 2010-02-13 13:17:02 | |
| 11 | KBS-6400 | 이*수 | ACD10-5909 | | | ✓ | 2010-02-13 13:19:54 | |
| 12 | KBS-6401 | 정*영 | ACD10-5910 | | | ✓ | 2010-02-13 13:24:23 | |
| 13 | KBS-6402 | 2*숙 | ACD10-5911 | | | ✓ | 2010-02-13 13:27:46 | |
| 14 | KBS-6403 | 한*윤 | ACD10-5912 | | | ✓ | 2010-02-13 13:31:37 | |
| 15 | KBS-6404 | 임*외 | ACD10-5913 | | | ✓ | 2010-02-13 13:34:53 | |

We request genetic analysis of the above identified samples.
February 13, 2010    Applicant: Jinguk KIM

FIG. 3

|          | 0.0350 | 0.0261 | 0.0000 | 0.0000 ng/ul | 260/280 |
|----------|--------|--------|--------|--------------|---------|
| ACD10-5763 | 0.0729 | 0.0526 | 0.0379 | 0.0265 | 1.90 | 1.43 |
| ACD10-5764 | 0.1398 | 0.0830 | 0.1048 | 0.0569 | 5.24 | 1.84 |
| ACD10-5765 | 0.1443 | 0.0958 | 0.1093 | 0.0697 | 5.47 | 1.57 |
| ACD10-5766 | 0.0874 | 0.0634 | 0.0524 | 0.0373 | 2.62 | 1.40 |
| ACD10-5816 | 0.1046 | 0.0669 | 0.0696 | 0.0408 | 3.48 | 1.71 |
| ACD10-5817 | 0.1446 | 0.1087 | 0.1096 | 0.0826 | 5.48 | 1.33 |
| ACD10-5818 | 0.1767 | 0.1103 | 0.1417 | 0.0842 | 7.09 | 1.68 |
| ACD10-5819 | 0.1205 | 0.0922 | 0.0855 | 0.0661 | 4.28 | 1.29 |
| ACD10-5820 | 0.2755 | 0.1554 | 0.2405 | 0.1293 | 12.03 | 1.86 |
| ACD10-5821 | 0.2181 | 0.1214 | 0.1831 | 0.0953 | 9.16 | 1.92 |
| ACD10-5822 | 0.1807 | 0.1058 | 0.1457 | 0.0797 | 7.29 | 1.83 |
| ACD10-5823 | 0.1591 | 0.1042 | 0.1241 | 0.0781 | 6.21 | 1.59 |
| ACD10-5824 | 0.2312 | 0.1367 | 0.1962 | 0.1106 | 9.81 | 1.77 |
| ACD10-5825 | 0.1110 | 0.0784 | 0.0760 | 0.0523 | 3.80 | 1.45 |
| ACD10-5826 | 0.2016 | 0.1186 | 0.1666 | 0.0925 | 8.33 | 1.80 |
| ACD10-5827 | 0.1046 | 0.0722 | 0.0696 | 0.0461 | 3.48 | 1.51 |
| ACD10-5828 | 0.1686 | 0.1036 | 0.1336 | 0.0775 | 6.68 | 1.72 |
| ACD10-5829 | 0.0913 | 0.0697 | 0.0563 | 0.0436 | 2.82 | 1.29 |

100213

FIG. 5 report on genetic analysis results

1. client institution

| institution | | | department | | |
|---|---|---|---|---|---|
| address | | | | | |
| Tel | | | HP | | |
| Fax | | | E-mail | | |

2. testing institution

| institution | | | department | | |
|---|---|---|---|---|---|
| address | 서울시 강남구 역삼동 819-7번지 오피스텔 동 6층 | | | | |
| Tel | 02501-9834(교환번호) | | HP | | |
| Fax | 02501-1445 | | E-mail | Avellino@avellino.co.kr | |

3. information about samples

4. information about test

| No. | Sample ID | subject's name | analysis code | kind of sample | | | day and time of collection | day and time of test | DNA extraction results | AGDS™ | | analysis results | remarks |
|---|---|---|---|---|---|---|---|---|---|---|---|---|---|
| | | | | blood (ml) | epidermis (swab) | hair root (number) | | | | X-axis | Y-axis | | |
| 1 | 5821 | 김*0116 | ACD10-5852 | | √ | | 2010-02-12 11:01:36 | 2010-02-13 | 적합 | 0.54 | 0.07 | Normal | C1 |
| 2 | 5822 | 김*0116 | ACD10-5853 | | √ | | 2010-02-12 11:02:18 | 2010-02-13 | 적합 | 0.53 | 0.07 | Normal | C1 |
| 3 | 5823 | 김*0110 | ACD10-5854 | | √ | | 2010-02-12 11:37:00 | 2010-02-13 | 적합 | 0.52 | 0.07 | Normal | C1 |
| 4 | 324 | 김*0116 | ACD10-5855 | | √ | | 2010-02-12 11:38:15 | 2010-02-13 | 적합 | 0.54 | 0.08 | Normal | C1 |
| 5 | 5825 | 김*0116 | ACD10-5856 | | √ | | 2010-02-12 11:48:42 | 2010-02-13 | 적합 | 0.56 | 0.08 | Normal | C1 |
| 6 | 5827 | 김*29 | ACD10-5858 | | √ | | 2010-02-12 12:25:27 | 2010-02-13 | 적합 | 0.49 | 0.06 | Normal | C1 |
| 7 | 5828 | 김*16 | ACD10-5859 | | √ | | 2010-02-12 12:33:22 | 2010-02-13 | 적합 | 0.46 | 0.05 | Normal | C1 |
| C1 | Control1 | | | | | | | 2010-02-13 | | 0.42 | 0.05 | Normal | |
| C1 | Control2 | | | | | | | 2010-02-13 | | 0.32 | 0.22 | TGFBR124H-Hetero | |
| C1 | Control3 | | | | | | | 2010-02-13 | | 0.06 | 0.40 | TGFBR124H-Homo | |
| C1 | Control4 | | | | | | | 2010-02-13 | | 0.00 | 0.00 | NTC | |

Analysis results
Normal: no mutation appeared at position R124 of TGFBI gene
Mutation existed at position R124 of TGFBI gene (mutation existed in only one of parents); referred to as "Avellino hetero"
Mutation existed at position R124 of TGFBI gene (mutation existed in both parents); referred to as "Avellino homo"
NTC: Negative Control February 13, 2010     Chief analyzer: Jin LEE

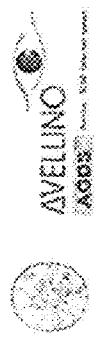

AVELLINO

FIG. 6

```
                       SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: Primer for amplifying 124th codon of TGFBI gene

<400> SEQUENCE: 1
tccaccacca ctcagctgta                                                  20

<210> SEQ ID NO 2
<211> LENGTH: 19
<212> TYPE: DNA
<213> ORGANISM: Artificial
<220> FEATURE:
<223> OTHER INFORMATION: Primer for amplifying 124th codon of TGFBI gene

<400> SEQUENCE: 2
ccatctcagg cctcagctt                                                   19

<210> SEQ ID NO 3
<211> LENGTH: 15
<212> TYPE: DNA
<213> ORGANISM: Artificial
<220> FEATURE:
<223> OTHER INFORMATION: Probe for detecting TGFBI gene whose 124th
      codon is "CGC"

<400> SEQUENCE: 3
cacggaccgc acgga                                                       15

<210> SEQ ID NO 4
<211> LENGTH: 15
<212> TYPE: DNA
<213> ORGANISM: Artificial
<220> FEATURE:
<223> OTHER INFORMATION: Probe for detecting TGFBI gene whose 124th
      codon is "CAC"

<400> SEQUENCE: 4
cacggaccac acgga                                                       15
```

SYSTEM FOR DIAGNOSING AVELLINO CORNEAL DYSTROPHY

CROSS-REFERENCE TO RELATED APPLICATIONS

This application is a U.S. national phase under the provisions of 35 U.S.C. § 371 of International Patent Application No. PCT/KR11/07272 filed Sep. 30, 2011, which in turn claims priority of Korean Patent Application No. 10-2010-0096103 filed Oct. 1, 2010. The disclosures of such international patent application and Korean priority patent application are hereby incorporated herein by reference in their respective entireties, for all purposes.

TECHNICAL FIELD

The present invention relates to a system for diagnosing Avellino corneal dystrophy, and more particularly to a system for diagnosing Avellino corneal dystrophy, in which whether a sample is normal or Avellino corneal dystrophy is determined based on the ratio of the input first PCR amplification value and the second PCR amplification value.

BACKGROUND ART

Corneal dystrophy is an autosomal dominant hereditary disease, which begins with an opacity in the center of cornea and gradually spreads and thus ends up vision loss as a patient gets older. It includes Avellino corneal dystrophy, Granular corneal dystrophy, lattice type I corneal dystrophy, Reis-bucklers corneal dystrophy, etc., and is caused by mutation of a gene coding βIG-H3 protein.

Heterozygous patients suffering from Avellino corneal dystrophy appear to have severe loss of vision as getting older and homozygous patients appear to have complete loss of vision since 6 years old. Avellino corneal dystrophy is a newly named disease in 1988, divided from generally called Granular corneal dystrophy because it was found to have genetic distinction. Also, it has been known to be the most common corneal dystrophy worldwide, 1/340 to 1/1000 of prevalence rate in Korea (the case of heterozygote) based on genetic analysis indicates that it is a common dystrophy (Holland, E. J. et al., Ophthalmology, 99:1564, 1992; Kennedy, S. M. et al., Br. J. Ophthalmol., 80:489, 1996; Dolmetsch, A. M. et al., Can. J. Ophthalmol., 31:29, 1996; Afshari, N. A. et al., Arch. Ophthalmol., 119:16, 2001; Stewart, H. S. Hum. Mutat., 14:126, 1999).

The present inventors have found that if a heterozygous Avellino corneal dystrophy patient has LASIK surgery, about 2 years later, opacity of cornea starts to develop aggressively and eventually results in vision loss (Jun, R M et al., Ophthalmolgy, 111:463, 2004). Previously, eye surgery has been performed with an expectation that LASIK or Excimer Laser surgery would get rid of vision blurriness of a patient suffering from corneal dystrophy. Also, even in Korea, approximately 3 hundred thousand cases of LASIK surgery have been performed, which leads to the assumption that 300 people lost their vision, based on 1/1000 of minimum estimation of heterozygous patients suffering from Avellino corneal dystrophy. Patients who have undergone LASIK surgery are mainly in their 20's and 30's carrying out productive activities; therefore, their vision loss causes serious troubles in both society and economics. In addition, after approval of LASIK surgery since the year 2000 in USA, Avellino corneal dystrophy patients who underwent LASIK surgery have been found to lose eye sight among African American, which infers that plenty of similar cases might be occurring throughout the world.

However, although accurate diagnosis of Avellino corneal dystrophy is required to prevent the progression of Avellino corneal dystrophy by LASIK surgery, the diagnosis of Avellino corneal dystrophy is just conducted by microscopic observation of corneal opacity, and thus often doctors miss latent symptoms of patients to perform LASIK surgery, which results in vision loss. Therefore, rapid and precise diagnosis of corneal dystrophy is desperately in need.

In addition, in conventional diagnosis, the results of diagnosis may vary depending on variables such as the skill of a doctor and the patient's condition. Thus, the development of diagnostic methods having improved reliability and accuracy has been required.

DISCLOSURE OF INVENTION

Accordingly, the present inventors have made extensive efforts to provide a new system for diagnosing corneal dystrophies, including Avellino corneal dystrophy, which are required to be accurately diagnosed before vision enhancement surgery. As a result, the present inventors have found that, when a first PCR amplification value measured by adding to a sample DNA a primer pair capable of amplifying exon 4 of a transforming growth factor b-induced (TGFBI) gene and a probe capable of detecting a TGFBI gene containing no mutation in exon 4 is compared with a second PCR amplification value measured by adding to the sample DNA the primer pair capable of amplifying exon 4 of the TGFBI gene and a probe capable of detecting a TGFBI containing a mutation in exon 4, if the first PCR amplification value is 5-9 times the second PCR amplification value, the sample DNA is normal, and if the ratio of the first PCR amplification value to the second PCR amplification value is 1:1.5-1.5:1, the sample DNA is an Avellino corneal dystrophy heterozygote, and if the second PCR amplification value is 5-9 times the first PCR amplification value, the sample DNA is an Avellino corneal dystrophy homozygote. Based on this finding, the present invention has been completed.

Technical Problem

It is an object of the present invention to provide a new system for diagnosing Avellino corneal dystrophy, which can diagnose Avellino corneal dystrophy simpler and more accurate manner without being influenced by the doctor's skill.

Technical Solution

To achieve the above object, the present invention provides a system for diagnosing Avellino corneal dystrophy, the system comprising:

(a) a client group comprising at least one client, which transmits information about a sample and a request for analysis through a network to a server comprising an input means to request a diagnostic service and receives and stores the data of determination of Avellino corneal dystrophy, which are transmitted from a server comprising an output means in response to the request;

(b) the input means for receiving the information about the sample, the request for analysis, a first PCR amplification value measured by adding to a sample DNA a primer pair capable of amplifying exon 4 of a transforming growth factor b-induced (TGFBI) gene and a probe capable of detecting a TGFBI gene containing no mutation in exon 4, and a second PCR amplification value measured by adding to the sample DNA the primer pair capable of amplifying exon 4 of TGFBI gene and a probe capable of detecting a TGFBI gene containing a mutation in exon 4;

(c) an analysis means wherein when the first PCR amplification value is 5-9 times the second PCR amplification value, the sample DNA is determined to be normal, when the ratio of the first PCR amplification value to the second PCR amplification value is 1:1.5-1.5:1, the sample DNA is determined to be an Avellino corneal dystrophy heterozygote, and when the second PCR amplification value is 5-9 times the first PCR amplification value, the sample DNA is determined to be an Avellino corneal dystrophy homozygote; and (d) the output means for outputting the results of determination from the analysis means.

The present invention also provides a computer readable medium or media comprising the above system for diagnosing Avellino corneal dystrophy.

The present invention also provides a computer comprising the above system for diagnosing Avellino corneal dystrophy.

The present invention also provides a method of diagnosing Avellino corneal dystrophy using either the above system for diagnosing Avellino corneal dystrophy or the above computer readable medium or media.

Other features and embodiments of the present invention will be more apparent from the following detailed descriptions and the appended claims.

BRIEF DESCRIPTION OF THE DRAWINGS

FIG. 1 is a process chart showing a method of diagnosing Avellino corneal dystrophy using PCR amplification data.

FIG. 2 shows online request information displayed on the system operator sever.

FIG. 3 shows the results of calculating the concentration and purity of DNA using raw data.

FIG. 5 is a screen illustrating a report on the results of genetic analysis for a medical institution.

FIG. 6 is a screen illustrating a report on the results of genetic analysis for an individual.

BEST MODE FOR CARRYING OUT THE INVENTION

Figure 4:
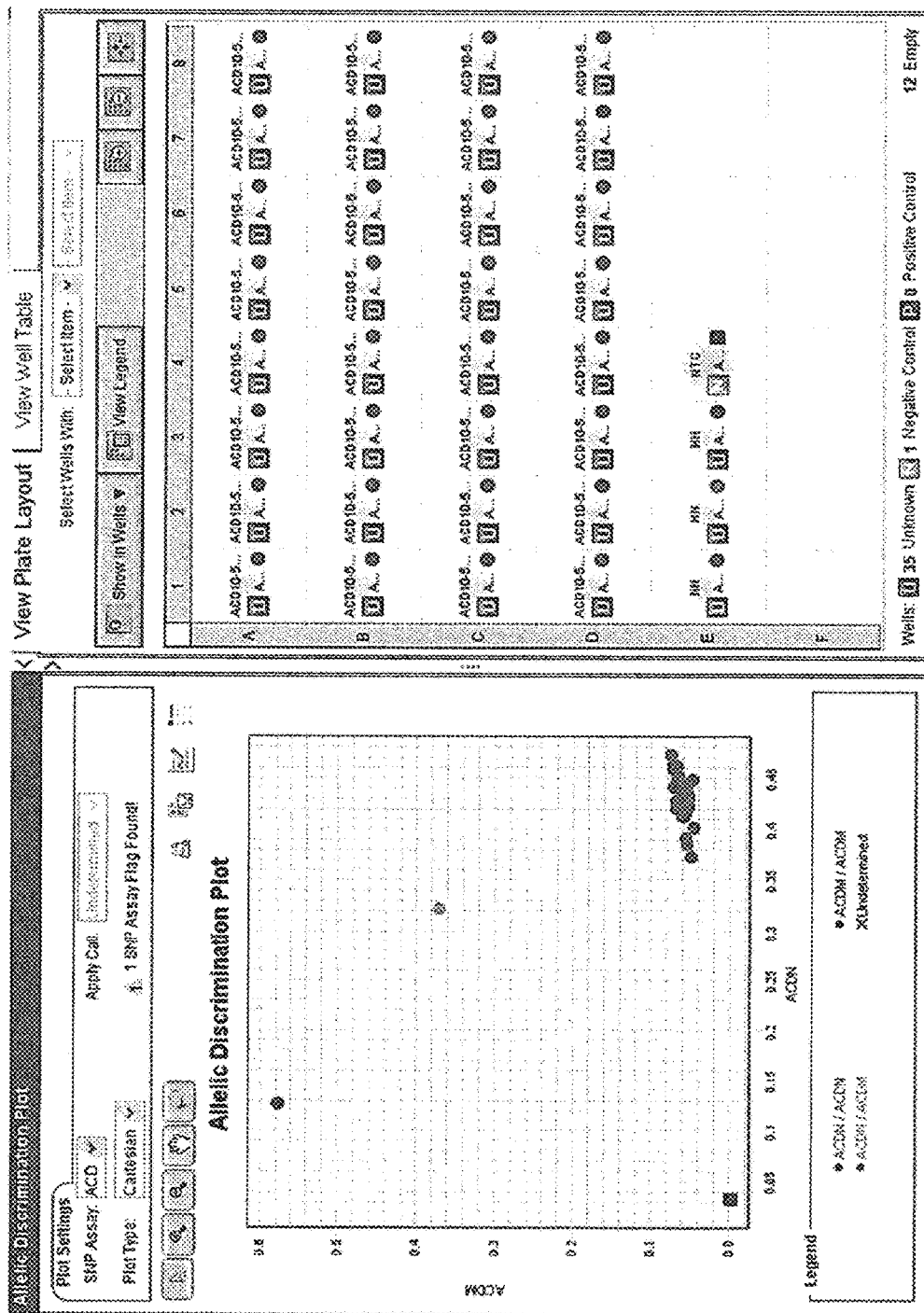
FIG. 4 shows an allelic discrimination plot, prepared using a first PCR amplification value and a second PCR amplification value, and a result table.

Unless defined otherwise, all technical and scientific terms used herein have the same meaning as commonly understood by one of ordinary skill in the art to which the invention pertains. Generally, the nomenclature used herein are well known and are commonly employed in the art.

The definition of main terms used in the detailed description of the invention is as follows.

As used herein, "Avellino corneal dystrophy" is also known as granular corneal dystrophy type II and is an autosomal dominant hereditary disease in which an opacity symptom occurs in the center of cornea. It is is a disease caused by genetic abnormality in which the sequence CGC in exon 4 of transforming a growth factor b-induced (TGFBI) gene is mutated to CAC so that the 124$^{th}$ amino acid arginine of BIGH3 protein is mutated to histidine (R124H).

As used herein, the term "heterozygote" refers to the case in which a mutation is present in only one gene of a pair of genes transmitted from parents. The term "Avellino corneal dystrophy heterozygote" refers to the case in which a mutation is present in only one of a pair of transforming growth factor b-induced (TGFBI) genes transmitted from parents.

As used herein, the term "homozygote" refers to the case in which a mutation is present in a pair of genes transmitted from parents. The term "Avellino corneal dystrophy homozygote" refers to the case in which a mutation is present in a pair of transforming growth factor b-induced (TGFBI) genes transmitted from parents.

As used herein, "a program" or "computer program" refers generally to a syntactic unit that conforms to the rules of a particular programming language and that is composed of declarations and statements or instructions, divisible into, "code segments" needed to solve or execute a certain function, task, or problem. A programming language is generally an artificial language for expressing programs.

As used herein, a "system" or a "computer system" generally refers to one or more computers, peripheral equipment, and software that perform data processing. A "user" or "system operator" in general includes a person, that uses a computer network accessed through a "user device" (e.g., a computer, a wireless device, etc.) for the purpose of data processing and information exchange. A "computer" is generally a functional unit that can perform substantial computations, including numerous arithmetic operations and logic operations without human intervention.

As used herein, a "computer readable medium" can be a hard disk, floppy disc, compact disc, magneto-optical disc, Random Access Memory, Read Only Memory or Flash Memory and the like, but is not limited thereto. In addition, the computer readable medium that is used in the present invention can be included in a single computer or distributed in a network. Herein, the network may be any conventional network system such as LAN (local area network) or WAN (wide area network). A network or a server, which may be used in the present invention, may be in the form of known network or server, such as World Wide Web application or World Wide Web server.

In one aspect, the present invention is directed to a system for diagnosing Avellino corneal dystrophy, the system comprising:

(a) a client group comprising at least one client, which transmits information about a sample and a request for analysis through a network to a server comprising an input means to request a diagnostic service and receives and stores the data of determination of Avellino corneal dystrophy, which are transmitted from a server comprising an output means in response to the request;

(b) the input means for receiving the information about the sample, the request for analysis, a first PCR amplification value measured by adding to a sample DNA a primer pair capable of amplifying exon 4 of a transforming growth factor b-induced (TGFBI) gene and a probe capable of detecting a TGFBI gene containing no mutation in exon 4, and a second PCR amplification value measured by adding to the sample DNA the primer pair capable of amplifying exon 4 of TGFBI gene and a probe capable of detecting a TGFBI gene containing a mutation in exon 4;

(c) an analysis means wherein when the first PCR amplification value is 5-9 times the second PCR amplification value, the sample DNA is determined to be normal, when the ratio of the first PCR amplification value to the second PCR amplification value is 1:1.5-1.5:1, the sample DNA is determined to be an Avellino corneal dystrophy heterozygote, and when the second PCR amplification value is 5-9 times the first PCR amplification value, the sample DNA is determined to be an Avellino corneal dystrophy homozygote; and (d) the output means for outputting the results of determination from the analysis means.

FIG. 1 is a process chart showing a method of diagnosing Avellino corneal dystrophy using PCR amplification data. Hereinafter, the present invention will be described with reference to FIG. 1.

Preferably, the system of the present invention may include a client group comprising at least one client, which transmits information about a sample and a request for analysis through a network to a server comprising an input means to request a diagnostic service and receives and stores the data of determination of Avellino corneal dystrophy, which are transmitted from a server comprising an output means in response to the request.

As information about the sample, one or more of the kind of sample, the client name, the client institution name, collection date, collection time, and contact may be input. The sample that is used herein may be one or more of an oral mucosa cell, blood, and a hair root. In addition, the request for analysis may include a written consent to genetic testing.

In addition, the absorbance at 260 nm and the absorbance at 280 nm of DNA of the sample can be input as data, and a first calculating means calculates the concentration and purity of the sample DNA based on the absorbance. Also, the system of the present invention may include a second calculating means that calculates the amounts of probes, a primer pair and distilled water in view of the total number of samples and a control group. Moreover, the calculated concentration and purity of the sample DNA may be used to determine the amount of the sample DNA.

The probes consist of a probe, which can detect a TGFBI gene containing no mutation in exon 4, and a probe which can detect a TGFBI gene containing a mutation in exon 4. The primer pair refers to a primer pair capable of amplifying exon 4 of the TGFBI gene. Meanwhile, as reagents for performing PCR, Taq polymerase, dNTP, $MgCl_2$, PCR buffer and the like may be used.

The primer pair capable of amplifying exon 4 of the TGFBI gene is a primer pair capable of amplifying the position of codon 124 of the TGFBI gene and is preferably a primer pair represented by SEQ ID NOS: 1 and 2. In addition, the probe capable of detecting the TGFBI gene containing no mutation in exon 4 is a probe capable of detecting a TGFBI gene containing "CGC" at codon 124 and is preferably a probe represented by SEQ ID NO: 3. In addition, the probe capable of detecting the TGFBI gene containing a mutation in exon 4 is a probe capable of detecting a TGFBI gene containing "CAC" at codon 124 and is preferably a probe represented by SEQ ID NO: 4.

Primer Pair for Amplifying Codon 124 of TGFBI Gene

```
SEQ ID NO: 1: 5'-TCCACCACCACTCAGCTGTA-3'

SEQ ID NO: 2: 5'-CCATCTCAGGCCTCAGCTT-3'
```

Probe for Detecting TGFBI Gene Containing "CGC" at Codon 124

```
SEQ ID NO: 3: 5'-CACGGACCGCACGGA-3'
```

Probe for Detecting TGFBI Gene Containing "CAC" at Codon 124

```
SEQ ID NO: 4: 5'-CACGGACCACACGGA-3'
```

The inventive system for diagnosing Avellino corneal dystrophy may further comprise a PCR device which outputs, based on the calculated amounts of the probes, the primer pair and distilled water, a first PCR amplification value, measured by adding to the sample DNA the primer pair capable of amplifying exon 4 of the transforming growth factor b-induced gene and the probe capable of the TGFBI gene containing no mutation in exon 4, and a second PCR amplification value measured by adding to the sample DNA the primer pair capable of amplifying exon 4 of the TGFBI gene and the probe capable of detecting the TGFBI containing a mutation in exon 4. The PCR device may comprise a real-time PCR program set up therein.

For rapid processing, the primer pair capable of amplifying exon 4 of the TGFBI gene, the probe capable of detecting the TGFBI gene containing no mutation in exon 4, and the probe capable of detecting the TGFBI gene containing a mutation in exon 4 are simultaneously added to the sample DNA to perform PCR, so that the first PCR amplification value and the second PCR amplification value can be simultaneously obtained.

The output first PCR amplification value and second PCR amplification value are input into the input means. When the first amplification value is determined to be 5-9 times the second PCR amplification value by an analysis means, the sample is determined to be normal, and when the ratio of the first PCR amplification value to the second PCR amplification value is 1:1.5-1.5:1, the sample is determined to be an Avellino corneal dystrophy heterozygote. Also, when the second PCR amplification value is 5-9 times the first PCR amplification value, the sample is determined to be an Avellino corneal dystrophy homozygote. Preferably, when the first PCR amplification value is 7-8 times the second PCR amplification value, the sample is determined to be normal, and when the second PCR amplification value is 7-8 times the first PCR amplification value, the sample is determined to be an Avellino corneal dystrophy homozygote.

The system of the present invention may further comprise a display means that provides a two-dimensional allelic discrimination plot in which the first PCR amplification value and the second PCR amplification value are plotted along two axes. In the two-dimensional allelic discrimination plot, the first PCR amplification value is plotted along the X-axis, and the second PCR amplification value is plotted along the Y-axis. When the PCR amplification values are located at the right lower portion of the plot, the sample is determined to be normal, and when the PCR amplification values are located at the left upper portion of the plot, the sample is determined to be an Avellino corneal dystrophy homozygote.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Example of Diagnosis of Avellino Corneal Dystrophy 1-1: Input of Information About Sample and Request for Analysis A client group consisting of an individual client or a medical institution in which samples are collected from individual clients transmits information about a sample and a request for analysis to the system's operator server.

Herein, as the information on the sample, the kind of sample, the client's name, the institution's name, collection date, collection time, contact and so on are input, and the kind of sample is selected from whole blood, oral epidermis, and hair roots according the collected form. In addition, before the request for analysis is prepared, a written consent to genetic testing is prepared.

Information about an online request displayed on the system operator's server is as shown in FIG. 2.

1-2: Calculation of Concentration and Purity of Sample DNA

The system for diagnosing Avellino corneal dystrophy according to the present invention includes a first calculating means for calculating the concentration and purity of sample DNA.

A Genios instrument (TECAN, Austria) capable of measuring the absorbance at 260 nm and the absorbance at 280 nm of sample DAN may be connected to the system of the present invention. The XFluor4 program (TECAN, Austria) is executed in the system operator's apparatus (computer) connected to the instrument to measure the absorbance and calculate the concentration and purity of DNA.

Specifically, in 'XFluor4->Edit->Measurement parameter', 'Absorbance' is selected. Then, in 'Meas.params', the absorption wavelength is set at 260 nm, and 'Number of reads' is set at about 2, after which the OK button is clicked. Then, when 'XFluor4->Start measurement' is clicked, the absorbance at 260 nm is measured.

Meanwhile, in 'XFluor4->Edit->Meas.params', the absorption wavelength is set at 280 nm, and 'Number of reads' is set at about 2, after which the OK button is clicked. Then, when 'XFluor4->Start measurement' is clicked, the absorbance at 280 nm is measured.

At $OD_{260}=1$, the concentration of double-stranded DNA corresponds to about 50 ng/ul. Thus, the concentration of DNA is calculated by subtracting a blank value from the value at 260 nm and multiplying the subtracted value by 50. Also, after the absorbance at 260 nm and 280 nm has been measured, the purity of DNA can be determined based on the ratio of both ($OD_{260}/OD_{280}$). Generally, when the ratio of $OD_{260}/OD_{280}$ is between 1.8 and 2.0, the DNA is determined to have good purity.

FIG. 3 shows the results of calculating the concentration and purity of DNA using raw data.

1-3: Calculation of Amounts of Sample for PCR Amplification, Primer Pair, Distilled Water and the Like, and Output of PCR Amplification Values The system for diagnosing Avellino corneal dystrophy according to the present invention comprises a second calculating means for calculating the amount of sample DNA for PCR amplification and a PCR device.

The amounts of probes, a primer pair and distilled water were calculated before preparation by adding up the number of samples and a control normal (NN) group, an Avellino corneal dystrophy heterozygote (HN), an Avellino corneal dystrophy homozygote (HH) and a negative control (NTC), and then adding 0.2 µl to reduce the loss. The amount of sample DNA was determined based on the calculated concentration and purity of the sample DNA.

A primer pair for amplifying a mutation region (i.e., codon 124 position) of exon 4 of the TGFBI gene, a probe binding to a normal gene fragment having a mutation (i.e., a probe for detecting a TGFBI gene containing "CGC" at codon 124), and a probe binding to a gene fragment containing a mutation (i.e., a probe for detecting a TGFBI gene containing "CAC" at codon 124) are as follows. Herein, the probe binding to the normal gene fragment having no mutation was labeled with VIC, and the probe binding to the gene fragment having a mutation was labeled with FAM. In addition, a minor groove binder (MGB) was attached to facilitate binding to a complementary gene fragment.

Primer Pair for Amplifying Codon 124 Position of TGFBI Gene

SEQ ID NO: 1: 5'-TCCACCACCACTCAGCTGTA-3'

SEQ ID NO: 2: 5'-CCATCTCAGGCCTCAGCTT-3'

Probe for Detecting TGFBI Gene Containing "CGC" at Codon 124

SEQ ID NO: 3: 5'-CACGGACCGCACGGA-3'

Probe for Detecting TGFBI Gene Containing "CAC" at Codon 124

SEQ ID NO: 4: 5'-CACGGACCACACGGA-3'

Then, to obtain PCR values from the PCR device (Applied Biosystems), a real-time PCR program is executed. Specifically, when step-one software V2.0 in the RT-PCR device is double-clicked and 'Advanced setup' is clicked, 'Experiment Properties' appears. Then, 'Step One™ Instrument (48wells), Genotyping' is selected. In 'Plate Setup' under the 'Experiment Properties' line, 'ACD probe' is clicked for 'SNP Assay'. Line 1 of column A on a screen showing a 48-well plate is designated as ACD1, line 2 of column A is designated as ACD2, and in this manner, 48 wells are all designated. The number of cycles in 'Run Method' is changed to 36.

In a PCR reaction, a master mix consisting of 0.0625 µl of primers, 5 µl of probes, 2.9375 µl of distilled water and 2 µl of sample DNA was used. Experimental conditions were set up as follows.

Temperature Conditions

Pre-read: 60° C. for 30 sec;

Holding: 95° C. for 10 min;

Cyclying: 36 cycles, each consisting of 95° C. for 3-15 sec and 60° C. for 30-60 sec; and Post-read: 60° C. for 30 sec.

1-4: Determination of Avellino Corneal Dystrophy Based on PCR Amplification Values The VID positive value (first PCR amplification value measured by adding a primer pair for amplifying exon 4 of TGFBI gene and a probe binding to a normal gene fragment) and the FAM positive value (second PCR amplification value measured by adding a primer pair for amplifying exon 4 of TGFBI gene and a probe binding to a mutant gene fragment) in Example 1-3 were expressed in an allelic discrimination plot as shown in FIG. 4.

When the first PCR amplification value is determined to be 5-9 times the second PCR amplification value by the analysis means of the inventive system, the sample DNA is determined to be normal. When the ratio of the first PCR amplification value to the second PCR amplification value is 1:1.5-1.5:1, the sample DNA is determined to be a Avellino corneal dystrophy heterozygote, and when the second PCR amplification value is 5-9 times the first PCR amplification value, the sample DNA is determined to be an Avellino corneal dystrophy homozygote. Whether the sample is normal is expressed as a color on the left of FIG. 4.

Figure 6:
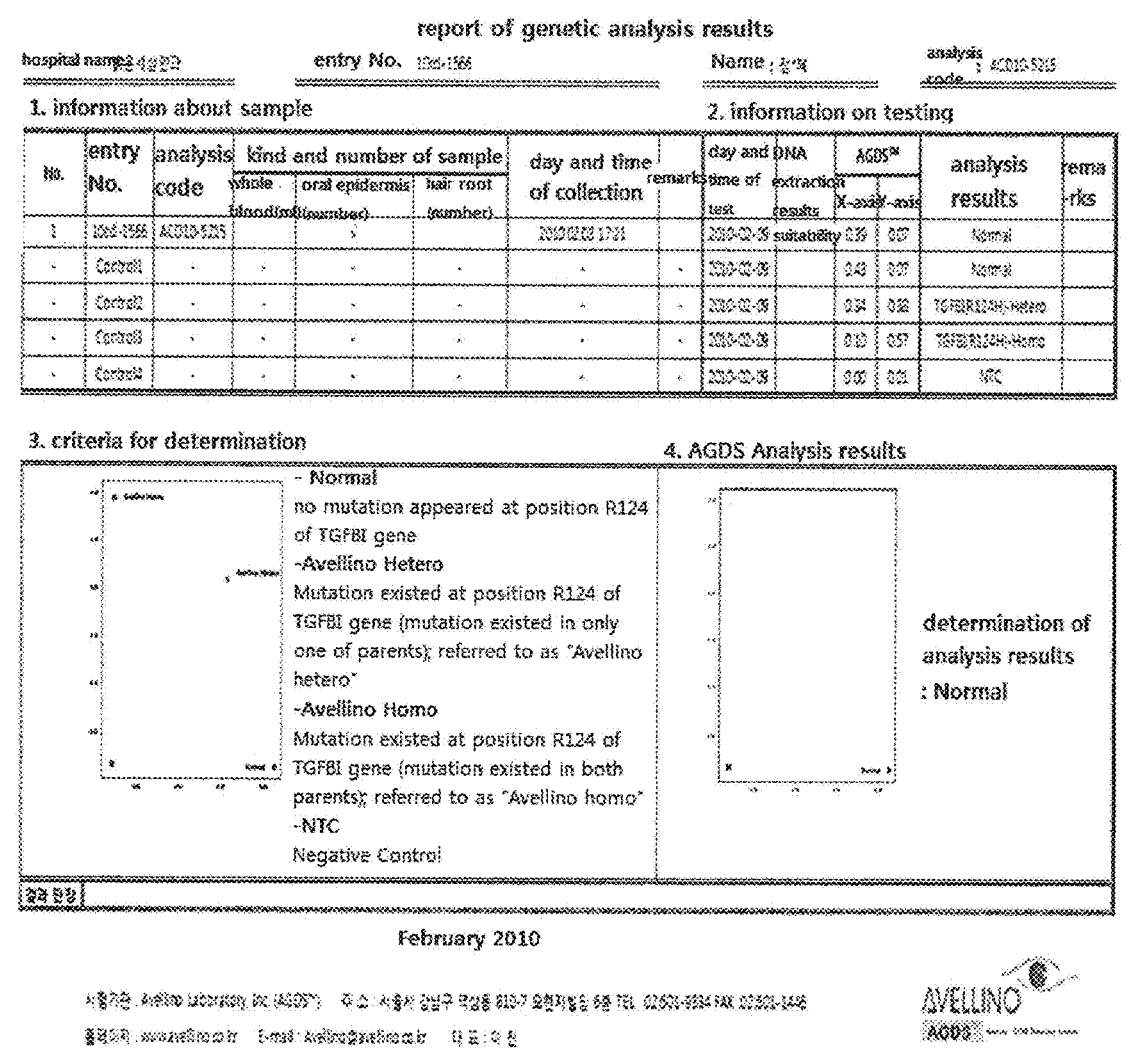

1-5: Output and Transmission of Results of Determination of Avellino Corneal Dystrophy The results of determination in Example 1-4 are output on a screen as shown in FIG. 5. The output results can be recorded for each individual as shown in FIG. 6. Such results are transmitted through the network to the client group from which information from the sample and the request for analysis were transmitted.

INDUSTRIAL APPLICABILITY

As described above, the system for diagnosing Avellino corneal dystrophy according to the present invention is a novel diagnostic system that can diagnose Avellino corneal dystrophy in a simpler and more accurate manner without being influenced by doctor's skill. Particularly, it makes the overall process systematic, and thus provides accurate diagnosis. In addition, the system can also easily administer a number of test subjects.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for predicting the risk of complication following laser eye surgery in a subject, the method comprising:
   detecting heterozygous Avellino corneal dystrophy in said subject by using a reaction mixture comprising:
      a first amplification primer and a second amplification primer for amplifying and determining a TGFβI gene sequence comprising nucleotides encoding amino acid residue 124 from a biological sample from the subject,
         wherein the first amplification primer is represented by nucleotide sequence SEQ ID NO:1, and
         wherein the second amplification primer is represented by nucleotide sequence SEQ ID NO:2; and
      a first detection oligonucleotide probe and a second detection oligonucleotide probe,
         wherein the first detection oligonucleotide probe is configured to hybridize to the amplified TGFβI gene sequence comprising nucleotides encoding arginine at amino acid residue 124 in the encoded TGFβI protein, and the first detection oligonucleotide probe is attached to a first fluorescent label, and
         wherein the second detection oligonucleotide probe is configured to hybridize to the amplified TGFβI gene sequence comprising nucleotides encoding histidine at amino acid residue 124 in the encoded TGFβI protein, and the second detection oligonucleotide probe is attached to a second fluorescent label that is distinct from the first fluorescent label.

2. The method of claim 1, wherein the laser eye surgery comprises one of Lasik and Excimer laser surgery.

3. A reaction mixture for detecting heterozygous Avellino corneal dystrophy in a subject, the reaction mixture comprising:
   a first amplification primer and a second amplification primer for amplifying and determining a TGFβI gene sequence comprising nucleotides encoding amino acid residue 124 from a biological sample from the subject,
      wherein the first amplification primer is represented by nucleotide sequence SEQ ID NO:1, and
      wherein the second amplification primer is represented by nucleotide sequence SEQ ID NO:2; and
   a first detection oligonucleotide probe and a second detection oligonucleotide probe,
      wherein the first detection oligonucleotide probe is configured to hybridize to the amplified TGFβI gene sequence comprising nucleotides encoding arginine at amino acid residue 124 in the encoded TGFβI protein, and the first detection oligonucleotide probe is attached to a first fluorescent label, and
      wherein the second detection oligonucleotide probe is configured to hybridize to the amplified TGFβI gene sequence comprising nucleotides encoding histidine at amino acid residue 124 in the encoded TGFβI protein, and the second detection oligonucleotide probe is attached to a second fluorescent label that is distinct from the first fluorescent label.

4. The reaction mixture of claim 3, wherein the first detection oligonucleotide probe capable of detecting a TGFβI gene containing "CGC" at codon 124.

5. The reaction mixture of claim 3, wherein the second detection oligonucleotide probe is capable of detecting a TGFβI gene containing "CAC" at codon 124.

6. The reaction mixture of claim 5, wherein the probe capable of detecting a TGFβI gene containing "CAC" at codon 124 is a probe represented by SEQ ID NO: 4.

7. The reaction mixture of claim 3, wherein the first detection oligonucleotide probe is represented by a nucleotide sequence SEQ ID NO:3 and the second detection oligonucleotide probe is represented by nucleotide sequence SEQ ID NO:4.

8. A method for detecting Avellino corneal dystrophy with the reaction mixture of claim 3, the method comprising:
   amplifying a TGFβI gene sequence comprising nucleotides encoding amino acid residue 124 from a biological sample from a subject using the first amplification primer and the second amplification primer of the reaction mixture of claim 3;
   hybridizing a detection oligonucleotide probe, of the first detection oligonucleotide probe and the second detection oligonucleotide probe of the reaction mixture of claim 3, to the amplified TGFβI gene sequence comprising nucleotides encoding amino acid residue 124; and
   detecting a mutation in the TGFβI gene sequence at residue 124, wherein arginine is mutated to a histidine (R124H) in the encoded TGFβI protein.

9. The method of claim 8, wherein the biological sample is any one of an oral mucosa cell, blood, and a hair root.

10. The reaction mixture of claim 3, wherein the first detection oligonucleotide probe attached to the first label does not naturally occur and the second detection oligonucleotide probe attached to the second label does not naturally occur.

11. A system for diagnosing Avellino corneal dystrophy, the system comprising:
   a polymerase chain reaction (PCR) device that includes the reaction mixture of claim 3.

12. A method for diagnosing Avellino corneal dystrophy, comprising using the system for diagnosing Avellino corneal dystrophy of claim 11.

13. The system for diagnosing Avellino corneal dystrophy of claim 11, wherein the operations include concurrently measuring the first PCR amplification value and the second PCR amplification value.

14. The system of claim 11, further comprising:
   a server comprising a non-transitory computer readable storage medium storing instructions, which, when executed, cause the server to perform operations including:
      receiving information about a sample and a request for Avellino corneal dystrophy diagnostic analysis from a client system that is located remotely from the server; and
      subsequent to receiving the information about the sample and the request for Avellino corneal dystrophy diagnostic analysis, causing the PCR device to obtain PCR amplification values, wherein the PCR amplification values include:
         a first PCR amplification value that corresponds to a number of copies of transforming growth factor β-induced (TGFβI) gene, in the sample, containing no mutation in exon 4 as measured by adding to the sample the first amplification primer, the second amplification primer, and the first detection oligonucleotide probe, and
         a second PCR amplification value that corresponds to a number of copies of the TGFβI gene, in the sample, containing a mutation in exon 4 as detected using the second detection oligonucleotide probe as measured by adding to the sample the first amplification primer, the second amplification primer, and the second detection oligonucleotide probe.

15. The system of claim 14, wherein the non-transitory computer readable storage medium also stores instructions, which, when executed, cause the server to perform operations including:
  in accordance with a determination that the first PCR amplification value is 5-9 times the second PCR amplification value, sending to the client system information indicating that the sample DNA is normal;
  in accordance with a determination that the ratio of the first PCR amplification value to the second PCR amplification value is 1:1.5-1.5:1, sending to the client system information indicating that the sample DNA corresponds to an Avellino corneal dystrophy heterozygote; and,
  in accordance with a determination that the second PCR amplification value is 5-9 times the first PCR amplification value, sending to the client system information indicating that the sample DNA corresponds to an Avellino corneal dystrophy homozygote.

16. The system of claim 14, wherein the first PCR amplification value and the second PCR amplification value are simultaneously measured.

17. The system of claim 14, wherein the information about the sample is one or more of the kind of sample, the client name, the client institution name, collection date, collection time, and contact.

18. The system of claim 14, wherein the request for analysis comprises a written consent to genetic testing.

19. The system of claim 14, wherein the operations include calculating the concentration and purity of the sample DNA by inputting the absorbance at 260 nm and the absorbance at 280 nm of the sample DNA, and calculating the amounts of probes, the primer pair and distilled water.

20. The system for diagnosing Avellino corneal dystrophy of claim 11, further comprising a display that provides a two-dimensional representation of an allelic discrimination plot in which the first PCR amplification value and the second PCR amplification value are plotted along two axes.

* * * * *